(12) United States Patent
Lyons et al.

(10) Patent No.: US 6,540,393 B1
(45) Date of Patent: Apr. 1, 2003

(54) APPARATUS FOR PREPARING MICROPARTICLES USING IN-LINE SOLVENT EXTRACTION

(75) Inventors: Shawn L. Lyons, Cincinnati, OH (US); Steven G. Wright, Madeira, OH (US)

(73) Assignee: Alkermes Controlled Therapeutics Inc. II, Cambridge, MA (US)

(*) Notice: Subject to any disclaimer, the term of this patent is extended or adjusted under 35 U.S.C. 154(b) by 0 days.

(21) Appl. No.: 09/930,450

(22) Filed: Aug. 16, 2001

Related U.S. Application Data

(62) Division of application No. 09/438,659, filed on Nov. 12, 1999.

(51) Int. Cl.⁷ ................................................. B01F 15/02
(52) U.S. Cl. ..................... 366/181.5; 366/336; 366/348
(58) Field of Search ............................. 366/181.5, 336, 366/337, 338, 339, 348

(56) References Cited

U.S. PATENT DOCUMENTS

| | | | |
|---|---|---|---|
| 1,626,487 A | * 4/1927 | Warren | ..................... 366/181.5 |
| 3,523,906 A | 8/1970 | Vrancken et al. | |
| 3,655,166 A | * 4/1972 | Sauer et al. | |
| 3,691,090 A | 9/1972 | Kitajima et al. | |
| 3,737,337 A | 6/1973 | Schnoring et al. | |

(List continued on next page.)

FOREIGN PATENT DOCUMENTS

| | | |
|---|---|---|
| EP | 0 486 959 A1 | 5/1992 |
| WO | WO 89/03678 | 5/1989 |
| WO | WO 90/13361 | 11/1990 |
| WO | WO 94/10982 | 5/1994 |
| WO | WO 95/13799 | 5/1995 |
| WO | WO 97/41837 | 11/1997 |
| WO | WO 99/12549 | 3/1999 |

OTHER PUBLICATIONS

Koch Engineering Co., Inc., Static Mixing Technology advertisement, pp. 1–15.
Baker, J.R., "Motionless Mixers Stir Up New Uses," *Chemical Engineering Progress*, pp. 32–38 (Jun. 1991).
Mutsakis, M., et al., "Advances in Static Mixing Technology," *Chemical Engineering Progress*, pp. 42–48 (Jul. 1986).
Bodmeier, R., et al., International Journal of Pharmaceutics, 43:179–186 (1988).
Beck, L.R., et al., Biology of Reproduction, 28:186–195 (Feb. 1983).
Toyomi Sato et al., Pharmaceutical Research, 5:21–30 (1988).
Wen–I Li et al., Journal of Controlled Release, 37:199–214 (Dec. 1995).
H.V. Maulding et al., Journal of Controlled Release, 3:103–117 (Mar. 1986).
Hongkee Sah et al., Pharmaceutical Research, 13:360–367 (Mar. 1996).
R. Jalil et al., Journal of Microencapsulation, vol. 7, No. 3, Jul.–Sep. 1990, pp. 297–319.
B. Conti et al., "Use of polylactic acid for the preparation of microparticulate drug delivery systems," J. Microencapsulation, 1992, vol. 9, No. 2, pp. 153–166, XP 000259942.
Y.F. Maa et al., "Liquid–liquid emulsification by static mixers for use in microencapsulation," J. Microencapsulation, 1996, vol. 13, No. 4, pp. 419–433, XP 000589904.

*Primary Examiner*—Tony G. Soohoo
(74) *Attorney, Agent, or Firm*—Andrea G. Reister; Covington & Burling

(57) ABSTRACT

Apparatus and method for preparing microparticles using in-line solvent extraction. An emulsion is formed by combining two phases in a static mixer. The emulsion is combined with an extraction liquid in a blending static mixer. The outflow of the blending static mixer is combined with additional extraction liquid. The additional extraction liquid and the outflow of the blending static mixer can be combined in a vessel, or through the use of a static mixer manifold that includes a plurality of static mixers.

11 Claims, 4 Drawing Sheets

U.S. PATENT DOCUMENTS

| | | | |
|---|---|---|---|
| 3,773,098 A | * 11/1973 | Rock | 366/181.5 |
| 3,773,919 A | 11/1973 | Boswell et al. | |
| 3,779,518 A | * 12/1973 | Koepke et al. | 366/339 |
| 3,891,570 A | 6/1975 | Fukushima et al. | |
| 3,960,757 A | 6/1976 | Morishita et al. | |
| 4,026,817 A | * 5/1977 | Ciuti et al. | 366/338 |
| 4,050,676 A | * 9/1977 | Morishima et al. | 366/339 |
| 4,221,862 A | 9/1980 | Naito et al. | |
| 4,230,630 A | * 10/1980 | Mag et al. | 366/339 |
| 4,241,023 A | * 12/1980 | Wilke et al. | 366/339 |
| 4,334,884 A | * 6/1982 | Wilke et al. | |
| 4,384,975 A | 5/1983 | Fong | |
| 4,389,330 A | 6/1983 | Tice et al. | |
| 4,530,840 A | 7/1985 | Tice et al. | |
| 4,940,588 A | 7/1990 | Sparks et al. | |
| 5,066,436 A | 11/1991 | Komen et al. | |
| 5,076,705 A | * 12/1991 | Brickhouse et al. | 366/337 |
| 5,407,609 A | 4/1995 | Tice et al. | |
| 5,421,408 A | * 6/1995 | Stoisits et al. | |
| 5,478,564 A | 12/1995 | Wantier et al. | |
| 5,541,172 A | 7/1996 | Labric et al. | |
| 5,650,173 A | 7/1997 | Ramstack et al. | |
| 5,654,008 A | 8/1997 | Herbert et al. | |
| 5,656,299 A | 8/1997 | Kino et al. | |
| 5,670,093 A | * 9/1997 | Payne | |
| 5,688,801 A | 11/1997 | Mesens et al. | |
| 5,770,231 A | 6/1998 | Mesens et al. | |
| 5,792,477 A | 8/1998 | Rickey et al. | |
| 5,871,778 A | 2/1999 | Kino et al. | |
| 5,916,598 A | 6/1999 | Rickey et al. | |
| 5,945,126 A | 8/1999 | Thanoo et al. | |
| 5,965,168 A | 10/1999 | Mesens et al. | |
| 6,291,013 B1 | 9/2001 | Gibson et al. | |
| 6,331,317 B1 | * 12/2001 | Lyons et al. | 264/4.1 |
| 6,395,304 B2 | * 5/2002 | Lyons et al. | 264/4.1 |

* cited by examiner

APPARATUS FOR PREPARING MICROPARTICLES USING IN-LINE SOLVENT EXTRACTION

CROSS-REFERENCE TO RELATED APPLICATIONS

This application is related to application Ser. No. 09/438,659, filed Nov. 12, 1999, and application Ser. No. 09/828,849, filed Apr. 10, 2001, the entirety of each of which is incorporated herein by reference.

BACKGROUND OF THE INVENTION

1. Field of the Invention

The present invention relates to preparation of microparticles. More particularly, the present invention relates to a method and an apparatus for preparing microparticles using in-line solvent extraction.

2. Related Art

A variety of methods is known by which compounds can be encapsulated in the form of microparticles. It is particularly advantageous to encapsulate a biologically active or pharmaceutically active agent within a biocompatible, biodegradable wall forming material (e.g., a polymer) to provide sustained or delayed release of drugs or other active agents. In these methods, the material to be encapsulated (drugs or other active agents) is generally dissolved, dispersed, or emulsified, using stirrers, agitators, or other dynamic mixing techniques, in a solvent containing the wall forming material. Solvent is then removed from the microparticles and thereafter the microparticle product is obtained.

Development of a microencapsulation process suitable for commercial scale production typically requires scaling up, by multiple factors, a laboratory scale process and/or a pilot scale process. The scaled-up process will almost always require larger piping and higher flow rates, particularly when the scale factor is very large or if it is desired or necessary to keep process transfer times similar to the smaller scale processes. Scale-up into new, larger equipment is often unpredicatable and achieved in large measure through trial and error. However, the economic costs of large-scale trial and error experiments can be prohibitive.

One approach to aiding the scale-up process is to use a static mixer to form an emulsion, as disclosed in U.S. Pat. No. 5,654,008. In the method disclosed in U.S. Pat. No. 5,654,008, a first phase, comprising the active agent and the polymer, and a second phase are pumped through a static mixer into a quench liquid to form microparticles containing the active agent. The use of a static mixer to form the emulsion tends to make the scale-up more predictable and reliable than the scale-up of other dynamic-mixing processes for making microparticles. However, numerous trials and experiments are still required to completely and accurately scale-up, such as to commercial scale or by a factor of 20 or more, a process such as the one disclosed in U.S. Pat. No. 5,654,008.

Thus, there is a need in the art for an improved method and apparatus for preparing microparticles. There is a particular need in the art for an improved process that can be more quickly, reliably, and accurately scaled-up from a laboratory or pilot scale to a commercial scale. The present invention, the description of which is fully set forth below, solves the need in the art for such a method and apparatus.

SUMMARY OF THE INVENTION

The present invention relates to an apparatus and method for preparing microparticles. In one aspect of the invention, a method of preparing microparticles is provided. The method comprises:

preparing a first phase, the first phase comprising an active agent and a polymer;

preparing a second phase;

combining the first phase and the second phase in a first static mixer to form an emulsion;

combining the emulsion and a first extraction liquid in a second static mixer; and combining an outflow of the second static mixer with a second extraction liquid.

In one aspect of such a method, the outflow of the second static mixer flows into a vessel containing the second extraction liquid. In another aspect, the outflow of the second static mixer flows into a vessel, and the second extraction liquid is added to the vessel. The second extraction liquid can be added to the vessel either while the outflow of the second static mixer is flowing into the vessel, or after the outflow of the second static mixer has completed flowing into the vessel. In yet another aspect, the outflow of the second static mixer and the second extraction liquid can be combined in another static mixer.

In a further aspect of the present invention, another method for preparing microparticles is provided. The method comprises:

preparing a first phase, the first phase comprising an active agent and a polymer;

preparing a second phase;

combining the first phase and the second phase in a first static mixer to form an emulsion, the emulsion forming an outflow of the first static mixer;

combining the outflow of the first static mixer and a first portion of a starting volume of an extraction liquid in a second static mixer to form an outflow of the second static mixer;

dividing the outflow of the second static mixer to form at least two flow streams;

flowing each of the at least two flow streams through a separate third static mixer; and combining the at least two flow streams with a second portion of the extraction liquid.

In one aspect of such a method, the at least two flow streams flow into a vessel containing the second portion of the extraction liquid. In another aspect, the at least two flow streams and the second portion of the extraction liquid are combined in a fourth static mixer. In yet another aspect, the at least two flow streams and the second portion of the extraction liquid are combined in a fourth static mixer, and the combining step is repeated until the starting volume of the extraction liquid is depleted. The combining step may be repeated by continuing to combine the at least two flow streams and the extraction liquid in the fourth static mixer until the starting volume of the extraction liquid is depleted. Alternatively, the combining step may be repeated by combining the at least two flow streams and the extraction liquid in additional static mixers until the starting volume of the extraction liquid is depleted.

In a further aspect of the present invention, another method for preparing microparticles is provided. The method comprises:

preparing a first phase, the first phase comprising an active agent and a polymer;

preparing a second phase;

combining the first phase and the second phase in a first static mixer to form an emulsion, the emulsion forming an outflow of the first static mixer;

combining the outflow of the first static mixer and a first extraction liquid in a second static mixer to form an outflow of the second static mixer;

dividing the outflow of the second static mixer to form at least two flow streams;

flowing each of the at least two flow streams through a separate third static mixer; and combining the at least two flow streams with a second extraction liquid.

In yet a further aspect of the present invention, a microencapsulated active agent prepared by a method for preparing microparticles is provided. Such a method comprises:

preparing a first phase, the first phase comprising an active agent and a polymer;

preparing a second phase;

combining the first phase and the second phase in a first static mixer to form an emulsion;

combining the emulsion and a first extraction liquid in a second static mixer; and combining an outflow of the second static mixer with a second extraction liquid.

In yet a further aspect of the present invention, a microencapsulated active agent prepared by another method for preparing microparticles is provided. Such a method comprises:

preparing a first phase, the first phase comprising an active agent and a polymer;

preparing a second phase;

combining the first phase and the second phase in a first static mixer to form an emulsion, the emulsion forming an outflow of the first static mixer;

combining the outflow of the first static mixer and a first portion of a starting volume of an extraction liquid in a second static mixer to form an outflow of the second static mixer;

dividing the outflow of the second static mixer to form at least two flow streams;

flowing each of the at least two flow streams through a separate third static mixer; and combining the at least two flow streams with a second portion of the extraction liquid.

In still a further aspect of the present invention, a system for preparing microparticles is provided. The system includes a first and second pump, and a first static mixer in fluid communication with each of the pumps. One of the pumps is configured to pump an organic phase into the first static mixer. One of the pumps is configured to pump a continuous phase into the first static mixer. A manifold, comprising a plurality of static mixers, is in fluid communication with the first static mixer. A third pump, in fluid communication with the manifold, is configured to pump an extraction liquid. A second static mixer is in fluid communication with the manifold. An outflow of the first static mixer and the extraction liquid flow through the manifold and then through the second static mixer.

In another aspect, the system can include a third static mixer in fluid communication with the first static mixer and with the manifold. The outflow of the first static mixer and the extraction liquid are combined in the third static mixer, prior to flowing through the manifold. The system may also include a vessel in fluid communication with the second static mixer so that an outflow of the second static mixer flows into the vessel. A fourth pump may also be provided to pump the extraction liquid into the second static mixer.

Features and Advantages

It is a feature of the present invention that it can be used to prepare microparticles, including microparticles containing an active agent.

It is another feature of the present invention that it allows for parallel flow streams for the in-line solvent extraction.

Yet another feature of the present invention is the ability to easily use different extraction liquids during the process. The system can be configured to introduce such different extraction liquids at the appropriate time and processing point.

An advantage of the present invention is that it substantially reduces or eliminates the need for a separate quench or extraction tank that contains a large volume of quench liquid, to remove solvent, and to form hardened microparticles.

The present invention advantageously enables the controlled extraction of the polymer solvent from a polymer/active agent droplet to form microparticles containing the active agent. The process advantageously provides a level of solvent removal sufficient for commercial products. The process also advantageously provides high loading efficiency, making it particularly useful for commercial products.

The process of the present invention advantageously provides a more consistent processing environment than conventional processes for forming microparticles. The in-line solvent extraction method of the present invention allows the emulsion droplets to all be exposed to the same processing conditions. In contrast, in conventional processes using an extraction tank or vessel, the processing conditions change over time as the solvent is extracted from the emulsion droplets in the tank.

The consistent processing conditions and environment of the present invention advantageously result in a process that is less time-dependent or scale-dependent than alternative processes.

The present invention provides a method and apparatus that are particularly advantageous for scale-up. The parallel path manifold of the present invention allows for capacity increases from an established (single path) system without full-scale trial and error experiments in new and different equipment. The total flow rate can be increased from the single path system based upon the number of flow streams in the manifold.

BRIEF DESCRIPTION OF THE FIGURES

The present invention is described with reference to the accompanying drawings. In the drawings, like reference numbers indicate identical or functionally similar elements.

DETAILED DESCRIPTION OF TILE PREFERRED EMBODIMENTS

Overview

Figure 1:
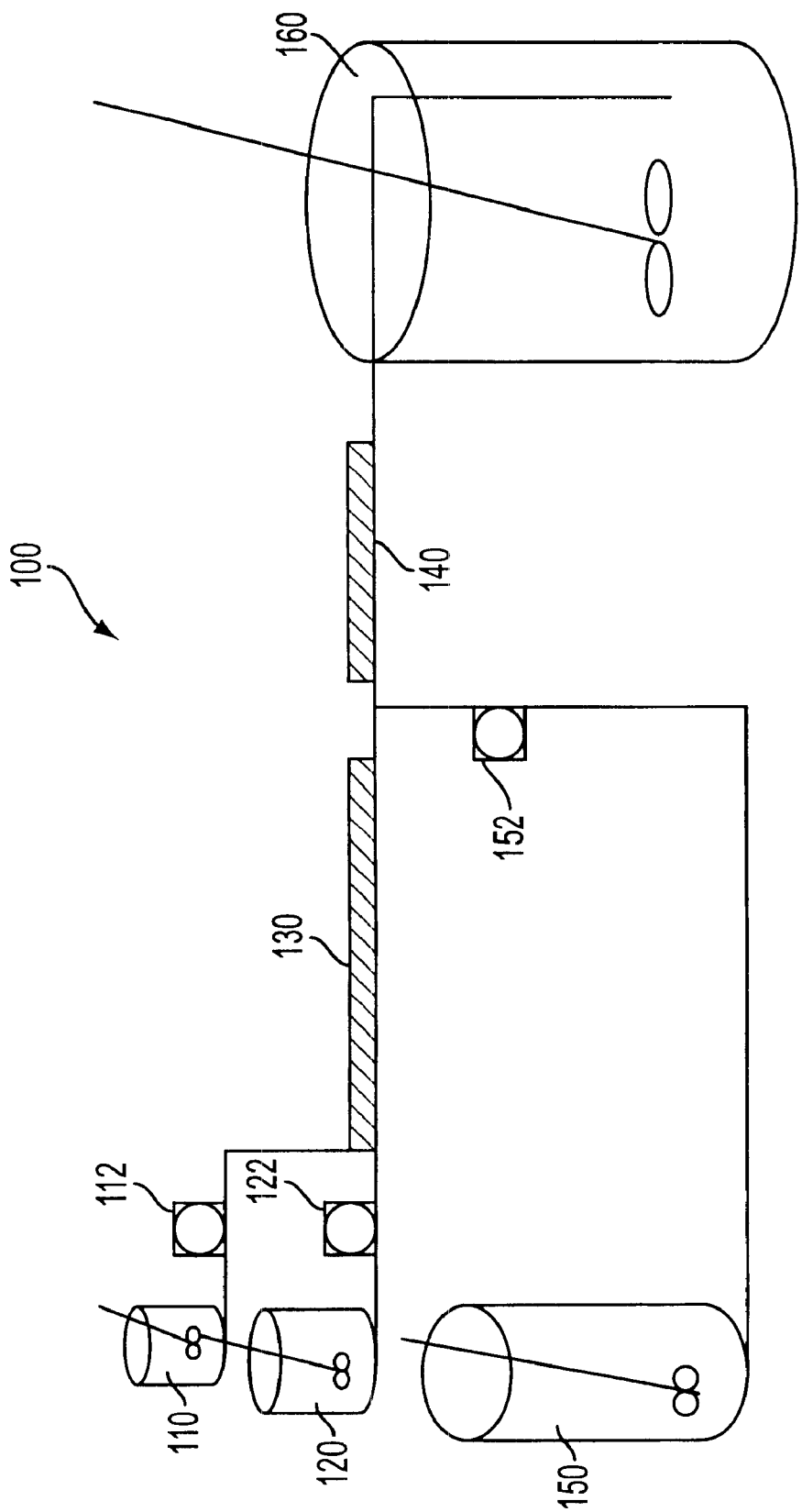
FIG. 1 shows one embodiment of an equipment configuration for preparing microparticles in accordance with the present invention.

The present invention provides an improved method and apparatus for preparing microparticles. The apparatus and methods of the present invention use in-line solvent extraction to provide a process that is more scalable, with less overall processing time, than conventional methods.

The methods of the present invention use a static mixer to combine a first phase, comprising an active agent and a polymer, with a second phase to form an emulsion. A process for forming an emulsion using a static mixer is described, for example, in U.S. Pat. No. 5,654,008, the entirety of which is incorporated herein by reference. The phase comprising the active agent and the polymer may be referred to herein as the "organic phase". The other phase may be referred to herein as the "continuous phase".

The outflow of the static mixer in which the emulsion is formed is combined with an extraction liquid in another static mixer that may be referred to herein as a "blending static mixer". In one embodiment, the outflow of the blending static mixer flows into a vessel where it is combined with additional extraction liquid that may be the same or different from the extraction liquid added to the blending static mixer. In another embodiment, the outflow of the blending static mixer is divided into a plurality of flow streams that flow through a manifold containing a plurality of static mixers. The plurality of flow streams are recombined downstream, and combined with additional extraction liquid. In a particularly preferred embodiment, the recombined flow streams and the additional extraction liquid are combined in another static mixer, and this combining step is repeated until the starting volume of the extraction liquid is depleted. Such an embodiment eliminates the need for an extraction tank for extracting solvent.

In the present invention a blending static mixer is used to combine the emulsion and the extraction liquid to form a combined flow stream. In one embodiment, the combined flow stream is divided into a plurality of flow streams for flow through the manifold. The use of the blending static mixer prior to the manifold is particularly advantageous because the emulsion and the extraction liquid may not be immediately miscible or homogeneous, making the division of the combined flow stream problematic. For multiphase streams such as the combined emulsion and extraction liquid, the use of the manifold without the blending static mixer could result in different compositions in each static mixer in the manifold. Because the combined emulsion and extraction liquid is not homogeneous, it would not divide evenly in conventional piping.

The manifold configuration of the present invention is particularly advantageous for scale-up. The parallel path manifold of the smaller diameter static mixers allows for capacity increases from an established (single path) system without full-scale trial and error experiments in new and different equipment. The total flow rate can be increased from the single path system based upon the number of flow streams in the manifold.

To ensure clarity of the description that follows, the following definitions are provided. By "microparticles" or "microspheres" is meant solid particles that contain an active agent or other substance dispersed or dissolved within a polymer that serves as a matrix or binder of the particle. The polymer is preferably biodegradable and biocompatible. By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weight" is meant parts by weight per total weight of microparticle. For example, 10 wt. % active agent would mean 10 parts active agent by weight and 90 parts polymer by weight. Unless otherwise indicated to the contrary, percentages (%) reported herein are by weight. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

METHOD AND EXAMPLES

The following examples are provided to explain the invention, and to describe the materials and methods used in carrying out the invention. The examples are not intended to limit the invention in any manner.

Example 1

Preparation of Risperidone Microparticles

Microparticles comprising risperidone were prepared at the one-kilogram scale.

The 1 Kg process (400 grams of active agent and 600 grams of polymer) provides a theoretical drug loading of the microparticles of 40% (400 grams/1000 grams×100%).

A 16.7% polymer solution was prepared by dissolving 600 grams of MEDISORB® 7525 DL polymer (Alkermes, Inc., Blue Ash, Ohio) in ethyl acetate. A 24% drug solution was prepared by dissolving 400 grams of risperidone base (Janssen Pharmaceutica, Beerse, Belgium) in benzyl alcohol. The organic phase was prepared by mixing the drug solution into the polymer solution. The continuous or aqueous phase was 30 Kg of a 1% polyvinyl alcohol (PVA) solution containing 6.5% ethyl acetate.

The emulsification step used two positive displacement pumps that fed the individual phases (one pump for the organic phase and one pump for the aqueous phase) to a connecting union where they were combined. A 5:1 aqueous phase to organic phase ratio was maintained throughout the emulsification step, at an average total flow rate of 3.2 Kg/min. Immediately following the connecting union in the processing stream was a ½ inch diameter in-line mixer, four feet in length. The exiting emulsion (outflow of the static mixer) was then mixed with an amount of a first extraction solution that was pumped via a peristaltic pump at an average flow rate of 9 Kg/min. The total volume of the first extraction solution that was transferred was 100 Kg.

The combined stream (diluted mixture of emulsion and first extraction solution) was then passed through a 1-inch diameter in-line static mixer (blending static mixer) 16 inches in length. The mixture was then passed through approximately 56 inches of transfer piping to reach 144 Kg of a second extraction solution contained in a stirred holding vessel. The mixture was stirred for 4 to 6 hours in the holding vessel. Samples were periodically taken to determine the levels of residual solvent(s), and to determine loading efficiency. Loading efficiency is the ratio, expressed as a percentage, of the actual drug loading to the theoretical drug loading.

Two experiments were done using the one-kilogram risperidone partial in-line extraction method described above. In Experiment One, the first and second extraction solutions both contained 2.5% ethyl acetate. In Experiment Two, the first extraction solution contained 2.5% ethyl acetate, and the second extraction solution was pure water.

The residual solvent levels and loading efficiencies obtained from the two experiments were compared to a control. The control was the average of four one-kilogram batches of risperidone microparticles prepared in the following manner. For each of the four control batches, the same steps were used to prepare the organic and aqueous phases as in the partial in-line extraction method described above, and the same emulsification step was also used. However, for each of the four control batches, the emulsion exiting the first static mixer was then transferred into a holding vessel that contained an aqueous extraction solution containing 2.5% ethyl acetate.

A comparison of the results obtained in Experiments One and Two with the risperidone control is shown below in Table 1. Table 1 shows the level of residual solvent for both ethyl acetate (Et/Ac) and benzyl alcohol (BA) for Experiments One and Two and the control. As shown in Table 1, the levels of residual solvent for Experiment One (3.6/5.1%) were comparable to the levels of residual solvent for the risperidone control (3.0/5.0%). In Experiment Two, the residual BA solvent level (9.5%) was significantly higher than the risperidone control BA solvent level (5.0%). The rate of extraction of each solvent is affected by the concentration of ethylacetate in the extraction solution, for example as described in U.S. Pat. No. 5,650,173, the entirety of which is incorporated therein by reference. The results obtained in Experiment Two for the residual benzyl alcohol level of 9.5% were comparable, however, to another risperidone control processed without an initial ethyl acetate component in the extraction solution, resulting in a residual benzyl alcohol level in the microparticles of 9.3%. The lower residual solvent level of ethyl acetate in Experiment Two (0.9%) is also likely the result of the lack of ethyl acetate in the second extraction solution.

TABLE 1

|  | Risperidone Process Partial In-Line Extraction | | Risperidone Control |
| --- | --- | --- | --- |
| Experiment # | One | Two | 1 kg Average |
| Residual Solvents (EtAc/BA) | 3.6/5.1% | 0.9/9.5% | 3.0/5.0% |
| Loading Efficiency | 92.2% | 88.0% | 93.2% |

As shown in Table 1, the loading efficiency of Experiment One (92.2%) was comparable to that of the risperidone control (93.2%). The 93.2% loading efficiency for the risperidone control is the loading efficiency of the final microparticle product after the residual solvent levels of ethyl acetate and benzyl alcohol are reduced to 1–2%. Loading efficiency for the same product containing 5–9% residual solvent levels of ethyl acetate and benzyl alcohol are expected to be lower due to mass balance. This is consistent with the results obtained in Experiment Two, with a lower loading efficiency of 88.0%.

Example 2

Preparation of Bupivacaine Microparticles

Microparticles comprising bupivacaine were prepared at the twenty-gram scale. The 20 gram process (4 grams of active agent and 16 grams of polymer) provides a theoretical drug loading of the microparticles of 20% (4 grams/20 grams×100%).

Sixteen grams of MEDISORB® 7525 DL polymer (Alkermes, Inc., Blue Ash, Ohio) and four grams of bupivacaine base were dissolved in 230 grams of ethyl acetate to make the organic phase. The aqueous phase consisted of a 1% PVA solution containing a saturating amount of polymer solvent (ethyl acetate), with a pH of 8.5 and a trizma buffer concentration of 0.05 molar. The extraction solution was a 0.05 molar trizma buffered aqueous solution at a pH of 8.5

The emulsification step used two positive displacement pumps that fed the individual phases (one pump for the organic phase and one pump for the aqueous phase) to a connecting union where they were combined. The organic phase pump operated at 75 ml/min, and the aqueous phase pump operated at 150 ml/min. A 3:1 aqueous phase to organic phase ratio was maintained throughout the emulsification step. Immediately following the connecting union was a ¼ inch diameter in-line static mixer, 17 and ½ inches in length. The exiting emulsion (outflow of the static mixer) was then mixed with an amount of the extraction solution that was pumped via a positive displacement pump at an extraction solution to emulsion ratio of 1:1. This extraction solution pump operated at 225 ml/min.

The combined stream (diluted mixture of emulsion and first extraction solution) was then passed through a ⅜-inch diameter in-line static mixer (blending static mixer) 4 and ¾ inches in length. Even though extraction of solvents is occurring in the blending static mixer, at this point in the process stream, the microdroplets of the emulsion have not fully hardened, and further processing is needed to ensure desired particle size. The outflow of the blending static mixer was divided into two flow streams, each then passing through a separate individual ¼ inch diameter in-line static mixer 6 inches in length. The two flow streams create less shear in each flow stream, tending to create microparticles of larger size. With only one large flow stream, there may be sufficient shear to result in smaller size microparticles. The two flow streams were then recombined, and added to a flow stream of the extraction solution that was pumped via a positive displacement pump operating at 450 ml/min. The resulting flow stream was passed through a ½ inch diameter in-line static mixer that was 12 inches in length, and then collected in an initially empty holding vessel. The two extraction solution pumps were started at the same time as the aqueous phase pump, and operated continuously.

After the organic phase had been exhausted, the contents in the holding vessel were gently mixed via an overhead agitator and the remaining extraction solution was transferred to the holding vessel. The mixture was agitated for an hour. The microparticles were recovered on a 25 micron screen, dried in a hood overnight, and analyzed for residual solvent level and loading efficiency.

The residual solvent level and loading efficiency obtained from the 20 gram bupivacaine process were compared to a 20 gram bupivacaine control. The 20 gram bupivacaine control was made using the same aqueous, organic, and extraction solution, and concentrations thereof, as in the bupivacaine in-line extraction method described above. The emulsification step was the same as described above, except for the use of a ¼ inch diameter, 16 inch long in-line static mixer to create the emulsion. The emulsion exiting this static mixer was then transferred into the total volume of the extraction solution that was contained in the stirred holding vessel.

A comparison of the results obtained using the bupivacaine in-line extraction method ("bupivacaine process") with the bupivacaine control is shown below in Table 2. As shown in Table 2, the level of residual solvent for the bupivacaine process is identical to the level of residual solvent for the bupivacaine control (4.2%). The loading efficiency for the bupivacaine process (75%) is comparable to the loading efficiency for the bupivacaine control (88.5%).

TABLE 2

|  | Bupivacaine Process In-Line Extraction | Bupivacaine Control |
| --- | --- | --- |
| Batch Size | 20 gram | 20 gram |
| Residual Solvent (EtAc) | 4.2% | 4.2% |
| Loading Efficiency | 75% | 88.5% |

Examples 1 and 2 demonstrate that the process of the present invention enables the controlled extraction of the polymer solvent from a polymer/active agent droplet to form microparticles containing the active agent. Each of the emulsion droplets are exposed to substantially the same processing conditions throughout the process. The initial hardening of the emulsion droplets is not time or scale-dependent, as in conventional encapsulation processes. The process of the present invention provides a level of solvent removal sufficient for commercial products. The process also provides high loading efficiency, making it particularly useful for commercial products.

Example 3

Methods for Preparing Microparticles

As exemplified by the examples discussed above, methods for preparing microparticles in accordance with the present invention will now be described in more detail. Exemplary apparatus suitable for carrying out such methods will be described below. In one embodiment of the present invention, a first phase, comprising an active agent and a polymer, is prepared. In one embodiment of the present invention, the first phase is prepared by dissolving the active agent in a first solvent to form an active agent solution. The polymer is dissolved in a second solvent to form a polymer solution. The active agent solution and the polymer solution are blended to form the first phase. In a particularly preferred embodiment, the active agent is selected from the group consisting of risperidone, 9-hydroxyrisperidone, and pharmaceutically acceptable salts thereof. In such an embodiment, a preferred first solvent is benzyl alcohol, and a preferred second solvent is ethyl acetate.

In another embodiment of the present invention, the first phase is prepared by dissolving the active agent and the polymer in a solvent to form a solution. In a particularly preferred embodiment, the active agent is bupivacaine, and the solvent is ethyl acetate. It should be understood that the present invention is not limited to any particular method or process by which the first phase is prepared, and other suitable processes would be readily apparent to one skilled in the art.

A second phase is prepared, and combined with the first phase in a first static mixer to form an emulsion. In a preferred embodiment, the two phases are pumped into the static mixer, with the second phase being pumped at a flow rate greater than the flow rate of the first phase. In one preferred embodiment, the ratio of the flow rate of the second phase to the flow rate of the first phase is approximately 2:1. Exemplary ratios of the volume of the second phase to the volume of the first phase are approximately 5:1 and approximately 3:1. However, it should be understood by one skilled in the art that the present invention is not limited to such a flow rate ratio or volume ratios, and other appropriate flow rate ratios and volume ratios would be readily apparent to one skilled in the art.

The emulsion is combined with a first extraction liquid in a second static mixer. In a preferred embodiment, the first extraction liquid is pumped at a first rate into the emulsion flowing out of the first static mixer to form a first combined stream. The first combined stream is then allowed to flow through the second static mixer. The volume ratio of the emulsion to the first extraction liquid can be approximately 1:1, although it should be readily apparent to one skilled in the art that other volume ratios can be used. In one embodiment, the second static mixer comprises a plurality of individual static mixers configured to provide a plurality of parallel flow streams. In a particularly preferred embodiment, the plurality of individual static mixers is two. However, it should be understood by one skilled in the art that the present invention is not limited to the use of two individual static mixers in such a configuration, and other appropriate numbers of individual static mixers would be readily apparent to one skilled in the art.

The outflow of the second static mixer is combined with a second extraction liquid. The second extraction liquid can be the same as, or different from, the first extraction liquid. The second extraction liquid can be the same as, or different from, the second phase. Similarly, the first extraction liquid can be the same as, or different from, the second phase.

In one embodiment of the present invention, the outflow of the second static mixer flows into a vessel that contains the second extraction liquid. In an alternate embodiment, the outflow of the second static mixer flows into the vessel, and the second extraction liquid is added to the vessel. The second extraction liquid can be added to the vessel either while the outflow of the second static mixer is flowing into the vessel, or after the outflow of the second static mixer has completed flowing into the vessel.

In a further embodiment of the present invention, the outflow of the second static mixer is combined with the second extraction liquid in a third static mixer. Preferably, the second extraction liquid is pumped at a second rate into the outflow of the second static mixer to form a second combined stream, and the second combined stream is allowed to flow through the third static mixer. In one embodiment, the second rate of pumping the second extraction liquid is greater than the first rate of pumping the first extraction liquid. However, the present invention is not limited to such pumping rates, and suitable pumping rates would be readily apparent to one skilled in the art.

The third static mixer can be an individual static mixer, a plurality of individual static mixers arranged in series, or a plurality of individual static mixers configured to provide a plurality of parallel flow streams. The outflow of the third static mixer flows into a vessel. The vessel can be empty prior to allowing the outflow of the third static mixer to flow therein. Alternatively, the vessel can contain an extraction liquid or other type of quench solution prior to allowing the outflow of the third static mixer to flow therein.

An alternate method for preparing microparticles in accordance with the present invention will now be described. A first phase, comprising an active agent and a polymer, is prepared. A second phase is prepared, and combined with the first phase in a first static mixer to form an emulsion, the emulsion forming an outflow of the first static mixer. Suitable methods and processes for preparing the first and second phases, and for combining in the first static mixer, have been described above and will not be repeated here for brevity.

The outflow of the first static mixer is combined with a first portion of a starting volume of an extraction liquid in a second static mixer to form an outflow of the second static mixer. The extraction liquid can be the same as, or different from, the second phase. The second static mixer can be an individual static mixer, a plurality of individual static mixers arranged in series, or a plurality of individual static mixers configured to provide a plurality of parallel flow streams.

The outflow of the second static mixer is divided to form at least two flow streams. Each of the at least two flow streams flows through a separate third static mixer. The separate third static mixer can be an individual static mixer, one of a plurality of individual static mixers arranged in series, or one of a plurality of individual static mixers configured to provide a plurality of parallel flow streams.

The at least two flow streams are combined with a second portion of the extraction liquid. In an alternate embodiment of the present invention, the at least two flow streams are combined with another extraction liquid different from the first portion of the extraction liquid. This other extraction liquid can be the same as, or different from, the second phase.

In one embodiment of the present invention, the at least two flow streams are combined with the second portion of the extraction liquid by allowing the at least two flow streams to flow into a vessel containing the second portion of the extraction liquid. In an alternate embodiment, the at least two flow streams are combined with the second portion of the extraction liquid in a fourth static mixer. The outflow of the fourth static mixer can then flow into a vessel. In a particularly preferred embodiment, the at least two flow streams are combined with the second portion of the extraction liquid in a fourth static mixer, and this combining step is continued until the starting volume of the extraction liquid is depleted.

Microparticles of the Present Invention

The microparticles prepared by the process of the present invention preferably comprise a polymeric binder, but it should be understood by one skilled in the art that the present invention is not limited to preparation of microparticles comprising a polymeric binder. Suitable polymeric binder materials include poly(glycolic acid), poly-d,1-lactic acid, poly-1-lactic acid, copolymers of the foregoing, poly (aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, polyphosphazines, albumin, casein, and waxes. Poly (d,1-lactic-co-glycolic acid) is commercially available from Alkerrnes, Inc. (Blue Ash, Ohio). A suitable product commercially available from Alkermes, Inc. is a 50:50 poly(d,1-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,1-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,1-PLA (Resomer® RG 206), and from Birmingham Polymers (Birmingham, Ala.). These copolymers are available in a wide range of molecular weights and ratios of lactic acid to glycolic acid.

One type of microparticle suitable for preparation by the present invention is a sustained-release microparticle that is biodegradable. However, it should be understood by one skilled in the art that the present invention is not limited to biodegradable or other types of sustained-release microparticles. As would be apparent to one skilled in the art, the molecular weight of the polymeric binder material for biodegradable microparticles is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric binder material being used, it is very difficult to specify an appropriate molecular weight range for all polymers. The molecular weight of the polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric binder bioerodes. By an appropriate selection of polymeric materials a microparticle formulation can be made in which the resulting microparticles exhibit both diffusional release and biodegradation release properties. This is usefull in according multiphasic release patterns.

The microparticles prepared in accordance with the present invention may include an active agent or other type of substance that is released from the microparticles into the host. Such active agents can include 1,2-benzazoles, more particularly, 3-piperidinyl-substituted 1,2-benzisoxazoles and 1,2-benzisothiazoles. The most preferred active agents of this kind are 3-[2-[4-(6-fluoro-1,2-benzisoxazol-3-yl)-1-piperidinyl]ethyl]-6,7,8,9-tetrahydro-2-methyl-4H-pyrido [1,2-a]pyrimidin-4-one ("risperidone") and 3-[2-[4-(6-fluro-1,2-benzisoxazol-3-yl)-1-piperidinyl]ethyl]-6,7,8,9-tetrahydro-9-hydroxy-2-methyl-4H-pyrido[1,2-a] pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents include non-steroidal antifertility agents; parasympathomimetic agents; psychotherapeutic agents; major tranquilizers such as chlorpromazine HCl, clozapine, mesoridazine, metiapine, reserpine, thioridazine and the like; minor tranquilizers such as chlordiazepoxide, diazepam meprobamate, temazepam and the like; rhinological decongestants; sedative-hypnotics such as codeine, phenobarbital, sodium pentobarbital, sodium secobarbital and the like; steroids such as testosterone and tesosterone propionate; sulfonamides; sympathomimetic agents; vaccines; vitamins and nutrients such as the essential amino acids; essential fats and the like; antimalarials such 4-aminoquinolines, 8-aminoquinolines, pyrimethamine and the like, anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocomine methanesulfonate, dihydroergokroyptine methanesulfate and combinations thereof; alkaloids such as atropine sulfate, Belladonna, hyoscine hydrobromide and the like; analgetics, narcotics such as codeine, dihydrocodienone, meperidine, morphine and the like; non-narcotics such as salicylates, aspirin, acetaminophen, d-propoxyphene and the like; antibiotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetracylines, and the like, anti-cancer agents; anti-convulsants such as mephenytoin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa; chlorambucil, cyclophosphamide, melphalan, nitrogen mustard, methotrexate and the like; antigens of such microorganisms as *Neisseria gonorrhea, Mycobacterium tuberculosis,* Herpes virus (homonis, types 1 and 2), *Candida albicans, Candida tropicalis, Trichomonas vaginalis, Haemophilus vaginalis,* Group B *Streptococcus ecoli, Mycoplasma hominis, Haemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis,* Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobacillus seminis, Mycoplasma bovigenitalium, Aspergillus fumigatus, Absidia ramosa, Trypanosoma equiperdum, Babesia caballi, Clostridium tetani,* and the like; antibodies that counteract the above microorganisms; and enzymes such as ribonuclease, neuramidinase, trypsin, glycogen phosphorylase, sperm lactic dehydrogenase, sperm hyaluronidase, adenosinetriphosphatase, alkaline phosphatase, alkaline phosphatase esterase, amino peptidase, trypsin, chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, and DPN-di-aprorasse.

Other suitable active agents include estrogens such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimesthisterone, megestrol acetate, chlormadinone acetate, norgestimate, norethisterone, ethisterone, melengestrol, norethynodrel and the like; and the spermnicidal compounds such as nonylphenoxypolyoxyethylene glycol, benzethonium chloride, chlorindanol and the like.

Still other suitable active agents include antifungals, antivirals, anticoagulants, anticonvulsants, antidepressants, antihistamines, hormones, vitamins and minerals, cardiovascular agents, peptides and proteins, nucleic acids, immunological agents, antigens of such bacterial organisms as *Streptococcus pneumoniae, Haemophilus influenzae, Staphylococcus aureus, Streptococcus pyogenes, Corynebacterium diphtheriae, Bacillus anthracis, Clostridium tetani, Clostridium botulinum, Clostridium perfringens, Streptococcus mutans, Salmonella typhi, Haemophilus parainfluenzae, Bordetella pertussis, Francisella tularensis, Yersinia pestis, Vibrio cholerae, Legionella pneumophila, Mycobacterium leprae, Leptospira interrogans, Borrelia burgdorferi, Campylobacter jejuni,* antigens of such viruses as smallpox, influenza A and B, respiratory syncytial, parainfluenza, measles, HIV, varicella-zoster, herpes simplex 1 and 2, cytomegalovirus, Epstein-Barr, rotavirus, rhinovirus, adenovirus, papillamavirus, poliovirus, mumps, rabies, rubella, coxsackjeviruses, equine encephalitis, Japanese encephalitis, yellow fever, Rift Valley fever, lymphocytic choriomeningitis, hepatitis B, antigens of such fungal protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydia psittaci, Chlamydia trachomatis, Plasmodium falciparum, Trypanosoma brucei, Entamoeba histolytica, Toxoplasma gondii, Trichomonas vaginalis, Schistosoma mansoni.* These antigens may be in the form of whole killed organisms, peptides, proteins, glycoproteins, carbohydrates, or combinations thereof.

Still other macromolecular bioactive agents that may be chosen for incorporation include, but are not limited to, blood clotting factors, hemopoietic factors, cytokines, interleukins, colony stimulating factors, growth factors, and analogs and fragments thereof.

The microparticles can be mixed by size or by type. However, it should be understood that the present invention is not limited to the use of biodegradable or other types of microparticles that contain an active agent. In one embodiment, the microparticles are mixed in a manner that provides for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

Apparatus

Turning now to FIG. 1, one embodiment of the apparatus of the present invention is shown (system 100). A first phase 110 and a second phase 120 are pumped via a pump 112 and a pump 122, respectively, into a first static mixer 130 to form an emulsion. The first phase preferably comprises an active agent and a polymer, and is preferably in the form of a solution. The second phase is preferably an aqueous solution that functions as the continuous phase of the emulsion.

A static or motionless mixer consists of a conduit or tube in which is received a number of static mixing elements. Static mixers provide uniform mixing in a relatively short length of conduit, and in a relatively short period of time. With static mixers, the fluid moves through the mixer, rather than some part of the mixer, such as a blade, moving through the fluid. Flow through one type of static mixer is illustrated in FIG. 3. A pump (not shown) introduces a stream of one or more fluids into a static mixer 10, as shown generally at 1. The stream is split and forced to opposite outside walls, as shown generally at 2. A vortex is created axial to the centerline of static mixer 10, as shown generally at 3. The vortex is sheared and the process recurs, but with the opposite rotation, as shown generally at 4. The clockwise/counterclockwise motion ensures a homogeneous product.

Figure 4:
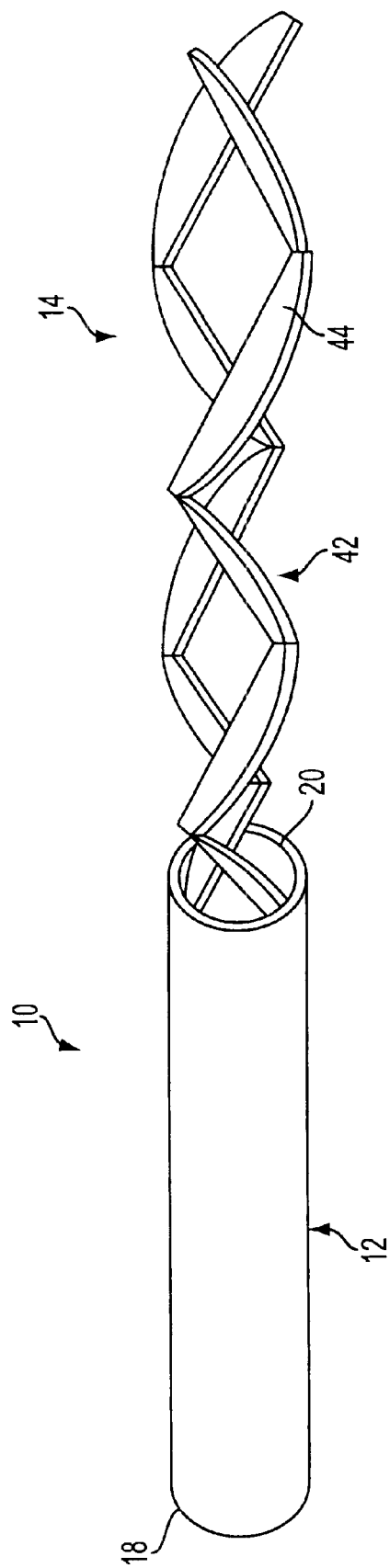
FIG. 4 shows a static mixer suitable for use with the present invention.

One example of a static mixer is shown in FIG. 4. Static mixer 10 includes a number of stationary or static mixing elements 14 arranged in a series within a conduit or pipe 12. The number of static mixing elements can range from 4 to 32 or more. Conduit 12 is circular in cross-section and open at opposite ends 18 and 20 for introducing and withdrawing fluids. Mixing element 14 comprises segments 42. Each segment 42 consists of a plurality of generally flat plates or vanes 44. The two substantially identical segments 42 are preferably axially staggered with respect to each other. A static mixer as shown in FIG. 4 is more fully described in U.S. Pat. No. 4,511,258, the entirety of which is incorporated herein by reference.

The emulsion is combined with a first extraction liquid 150, pumped via a pump 152, in a second static mixer 140. Static mixer 140 functions as a blending static mixer to blend the emulsion and the first extraction liquid. The outflow of second static mixer 140 flows into a vessel 160. In one embodiment of the present invention, vessel 160 contains a second extraction liquid. The second extraction liquid can be the same as, or different from, the first extraction liquid. In further embodiments of the invention, second phase 120 can be used as the first extraction liquid and/or the second extraction liquid.

In another embodiment of the present invention, the outflow of second static mixer 140 flows into vessel 160, and the second extraction liquid is added to vessel 160. The second extraction liquid can be added to vessel 160 either while the outflow of second static mixer 140 is flowing into vessel 160, or after the outflow of second static mixer 140 has completed flowing into vessel 160.

Static mixer 140 is shown in FIG. 1 as an individual static mixer. Alternatively, static mixer 140 could be configured as a manifold that includes a plurality of individual static mixers arranged in parallel to provide a plurality of parallel flow streams, as shown, for example, by manifold 240 illustrated in FIG. 2. Alternatively, static mixer 140 could be configured as a plurality of individual static mixers arranged in series. Similarly, static mixer 130 could also be configured as a manifold that includes a plurality of individual static mixers arranged in parallel, or as a series of individual static mixers. It should be understood by one skilled in the art that the present invention is not limited to the use of an individual static mixer for any of the elements depicted as individual static mixers in the Figures. As would be readily apparent to one skilled in the art, a plurality of individual static mixers arranged in series could be used, or a manifold containing a plurality of individual static mixers arranged in parallel to provide a plurality of parallel flow streams could also be used.

Figure 2:
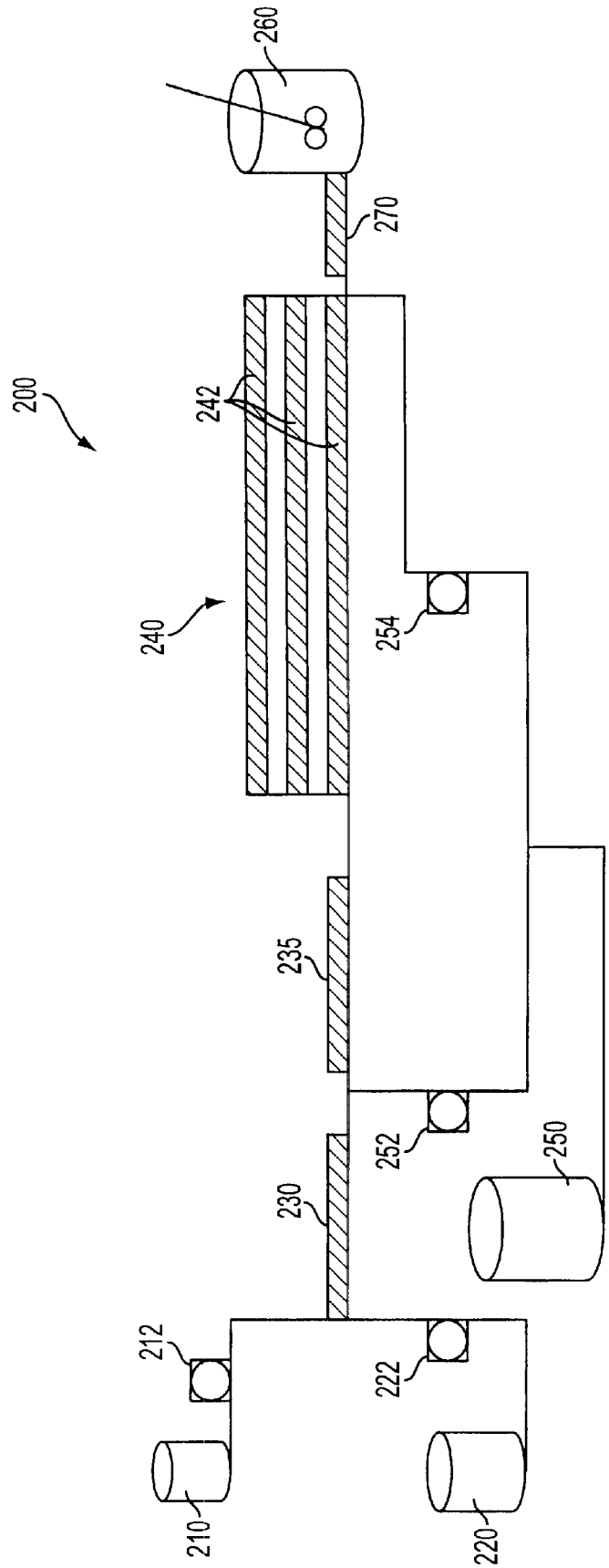
FIG. 2 shows another embodiment of an equipment configuration for preparing microparticles in accordance with the present invention.
Figure 3:
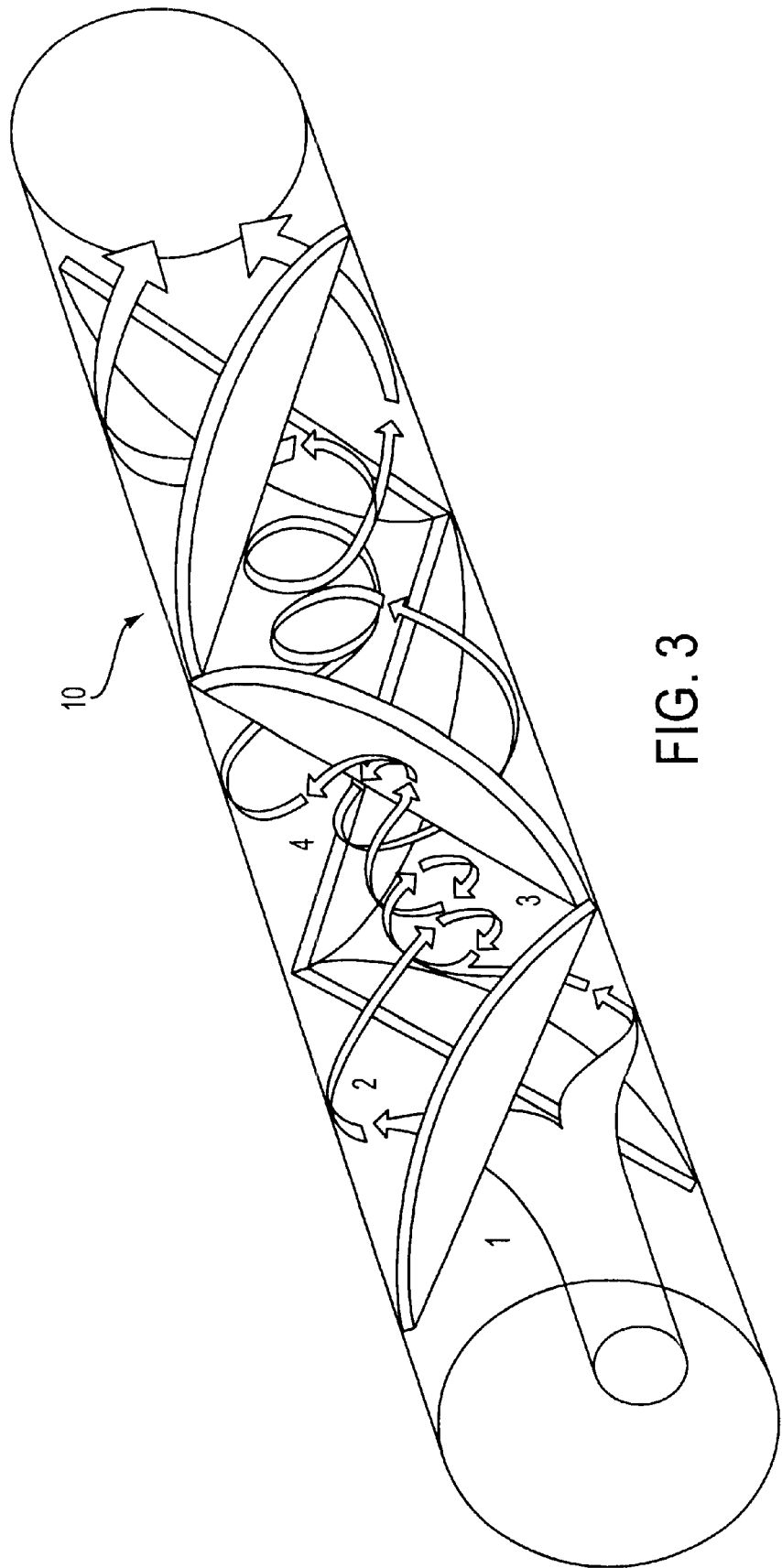
FIG. 3 illustrates flow through a static mixer.

Another embodiment of the invention is shown in FIG. 2 (system 200). A first phase 210 and a second phase 220 are pumped via a pump 212 and a pump 222, respectively, into a first static mixer 230 to form an emulsion. The first phase preferably comprises an active agent and a polymer, and is preferably in the form of a solution. The second phase is preferably an aqueous solution that functions as the continuous phase of the emulsion.

The emulsion is combined with a first portion of an extraction liquid 250, pumped via a pump 252, in a static mixer 235. Static mixer 235 functions as a blending static mixer to blend the emulsion and the first extraction liquid. The outflow of static mixer 235 is divided into a plurality of flow streams that flow into a manifold 240. Manifold 240 includes a plurality of individual static mixers 242 configured in a parallel arrangement that provides a plurality of parallel flow streams. Although FIG. 2 shows three individual and separate static mixers 242 in manifold 240, it should be readily apparent to one skilled in the art that manifold 240 can be configured with more, or less, individual static mixers 242. In a preferred embodiment, manifold 240 includes two individual static mixers 242, and the outflow of static mixer 235 is divided into two flow streams, each of the two flow streams flowing through one of the two individual static mixers.

The outflows of individual static mixers 242 are combined to form the outflow of manifold 240. The outflow of manifold 240 is combined with a second portion of extraction liquid 250, pumped via a pump 254, in another static mixer 270. In an alternate embodiment of the present invention, manifold 240 is replaced with a single static mixer located between static mixer 235 and static mixer 270. In yet another alternate embodiment, manifold 240 is replaced with a plurality of individual static mixers arranged in series. As would be readily apparent to one skilled in the art, static mixers 230, 235, and 270 depicted in FIG. 2 as individual static mixers could be replaced with a plurality of individual static mixers arranged in series, or with a manifold containing a plurality of individual static mixers arranged in parallel.

In one embodiment, pump 254 is configured to operate at a flow rate greater than a flow rate of pump 252. It should be understood that the present invention is not limited to such a flow rate configuration, and other suitable flow rates would be readily apparent to one skilled in the art.

The outflow of manifold 240 is combined with extraction liquid 250 in static mixer 270, and this combining is repeated until the starting volume of extraction liquid 250 is depleted. Once the starting volume of extraction liquid 250 is depleted, the outflow of static mixer 270 flows into a vessel 260 that is preferably initially empty, i.e., does not contain any extraction liquid. In this manner, all of extraction liquid 250 is introduced into the processing stream, and combined with the emulsion in one of the static mixers.

In system 200 as shown in FIG. 2, extraction liquid 250 is introduced into the processing stream at two different points via pumps 252 and 254. In an alternate embodiment of system 200, one type of extraction liquid could be introduced via pump 252, and a different type of extraction liquid could be introduced via pump 254. In a further embodiment, second phase 220 could be used as one or both of the extraction liquids introduced via pumps 252 and 254.

Alternatively, system 200 could be modified to eliminate static mixer 270 so that the outflow of manifold 240 flows into vessel 260 that contains the second portion of extraction liquid 250. System 200 could also be modified to add additional static mixers 270 in which additional portions of extraction liquid 250, or other different type of extraction liquid, are combined with the flow stream.

CONCLUSION

While various embodiments of the present invention have been described above, it should be understood that they have been presented by way of example only, and not limitation. The present invention is not limited to the preparation of controlled release microparticles, nor is it limited to a particular active agent, polymer or solvent, nor is the present invention limited to a particular scale or batch size. Thus, the breadth and scope of the present invention should not be limited by any of the above-described exemplary embodiments, but should be defined only in accordance with the following claims and their equivalents.

What is claimed is:

1. A system for preparing microparticles, comprising:

an organic phase source;

a continuous phase source;

an extraction liquid source;

a first pump in fluid communication with said organic phase source;

a second pump in fluid communication with said continuous phase source;

a first static mixer in fluid communication with said first pump and with said second pump, wherein said first pump is configured to pump organic phase from said organic phase source into said first static mixer, and said second pump is configured to pump continuous phase from said continuous phase source into said first static mixer;

a manifold in fluid communication with said first static mixer, said manifold comprising a plurality of individual static mixers configured to form a plurality of parallel flow streams, each of said plurality of parallel flow streams comprising at least one of said plurality of individual static mixers;

a third pump in fluid communication with said manifold, wherein said third pump is configured to pump extraction liquid from said extraction liquid source; and a second static mixer in fluid communication with said manifold, wherein an outflow of said first static mixer and the extraction liquid flow through said manifold through said plurality of parallel flow streams and then through said second static mixer.

2. The system of claim 1, further comprising:

a vessel in fluid communication with said second static mixer, wherein an outflow of said second static mixer flows into said vessel.

3. The system of claim 1, further comprising:

a fourth pump in fluid communication with said second static mixer, wherein said fourth pump is configured to pump the extraction liquid from said extraction liquid source into said second static mixer.

4. The system of claim 3, wherein said fourth pump is configured to operate at a flow rate greater than a flow rate of said third pump.

5. The system of claim 1, further comprising:

a third static mixer in fluid communication with said first static mixer and with said manifold, wherein the outflow of said first static mixer and extraction liquid from said extraction liquid source flow through said third static mixer prior to flowing through said manifold.

6. A system for preparing microparticles, comprising:

an organic phase source;

a continuous phase source;

an extraction liquid source;

a first pump in fluid communication with said organic phase source;

a second pump in fluid communication with said continuous phase source;

a first static mixer in fluid communication with said first pump and with said second pump, wherein said first pump is configured to pump organic phase from said organic phase source into said first static mixer, and said second pump is configured to pump continuous phase from said continuous phase source into said first static mixer;

a second static mixer in fluid communication with said first static mixer;

a third pump in fluid communication with said second static mixer, wherein said third pump is configured to pump extraction liquid from said extraction liquid source; and wherein an outflow of said first static mixer and the extraction liquid flow through said second static mixer.

7. The system of claim 6, further comprising:

a vessel in fluid communication with said second static mixer, wherein an outflow of said second static mixer flows into said vessel.

8. The system of claim 7, wherein said vessel is a second extraction liquid source.

9. The system of claim 8, wherein said second extraction liquid is different from the extraction liquid.

10. The system of claim 6, wherein said second static mixer is configured as a manifold that comprises a plurality of static mixers arranged in parallel.

11. The system of claim 6, wherein said second static mixer is configured as a manifold that comprises a plurality of static mixers.

* * * * *